US011951234B2

(12) United States Patent
Woods et al.

(10) Patent No.: US 11,951,234 B2
(45) Date of Patent: *Apr. 9, 2024

(54) DEODORIZING GLOVE HOLDER FOR ATHLETIC GLOVES AND OTHER EQUIPMENT

(71) Applicants: Krista Woods, Ashburn, VA (US); Christopher Woods, Ashburn, VA (US)

(72) Inventors: Krista Woods, Ashburn, VA (US); Christopher Woods, Ashburn, VA (US)

(*) Notice: Subject to any disclaimer, the term of this patent is extended or adjusted under 35 U.S.C. 154(b) by 508 days.

This patent is subject to a terminal disclaimer.

(21) Appl. No.: 17/191,133

(22) Filed: Mar. 3, 2021

(65) Prior Publication Data

US 2021/0275711 A1 Sep. 9, 2021

Related U.S. Application Data

(63) Continuation of application No. 15/626,257, filed on Jun. 19, 2017, now Pat. No. 10,967,089, which is a continuation of application No. 14/856,616, filed on Sep. 17, 2015, now abandoned.

(60) Provisional application No. 62/147,837, filed on Apr. 15, 2015, provisional application No. 62/052,110, filed on Sep. 18, 2014.

(51) Int. Cl.
*A61L 2/238* (2006.01)
*A61L 9/00* (2006.01)
*A61L 9/014* (2006.01)
*A61L 9/22* (2006.01)

(52) U.S. Cl.
CPC ............... *A61L 9/00* (2013.01); *A61L 2/238* (2013.01); *A61L 9/014* (2013.01); *A61L 9/22* (2013.01); *A61L 2202/26* (2013.01)

(58) Field of Classification Search
CPC .................................................. A61L 2202/26
See application file for complete search history.

(56) References Cited

U.S. PATENT DOCUMENTS

| | | |
|---|---|---|
| 2,446,904 A | 8/1948 | Harold |
| 4,401,770 A | 8/1983 | Hance |
| 4,742,580 A | 5/1988 | Phillips, Jr. et al. |
| 5,291,669 A | 3/1994 | Khoury et al. |
| 6,378,224 B1 | 4/2002 | Qualkinbush |
| 6,675,421 B1 | 1/2004 | Hsu |
| 2002/0127402 A1 | 9/2002 | Green et al. |
| 2007/0086914 A1 | 4/2007 | Antinozzi |
| 2008/0032119 A1 | 2/2008 | Feldhahn |
| 2011/0061257 A1 | 3/2011 | Balsillie |

(Continued)

FOREIGN PATENT DOCUMENTS

KR 20100082208 7/2010

OTHER PUBLICATIONS

Parachute Cord. Wilipedia. Archived version from Aug. 29, 2013.

(Continued)

*Primary Examiner* — Donald R Spamer
(74) *Attorney, Agent, or Firm* — Sughrue Mion, PLLC

(57) ABSTRACT

A deodorizer for insertion into athletic and other equipment, having an outer housing that is infused with an antimicrobial agent and that has ventilation holes, and containing a moisture absorbing deodorizer within the outer housing. The deodorizer absorbs moisture that allows bacteria to grow and the antimicrobial infused outer housing kills existing bacteria, thereby reducing bacteria and odor.

17 Claims, 7 Drawing Sheets

(56) References Cited

U.S. PATENT DOCUMENTS

2011/0293484 A1 12/2011 Stausgaard
2013/0230431 A1 9/2013 Mirowski

OTHER PUBLICATIONS

Scented Silica Gel. Silicagelpackets.com. Wayback Machine Capture from Nov. 12, 2011.
Silica Gel. Wikipedia. Archived version from Jul. 19, 2013.

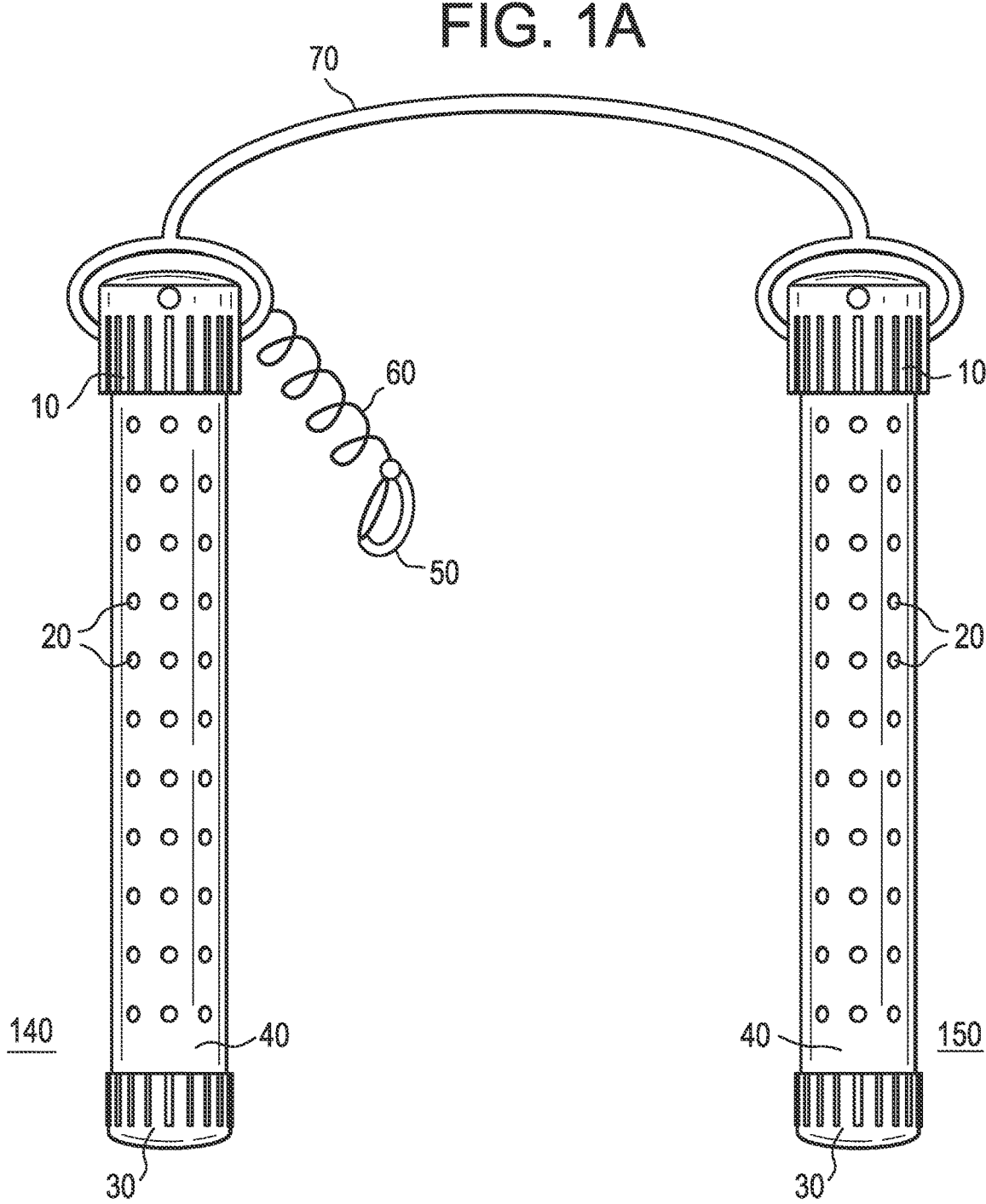
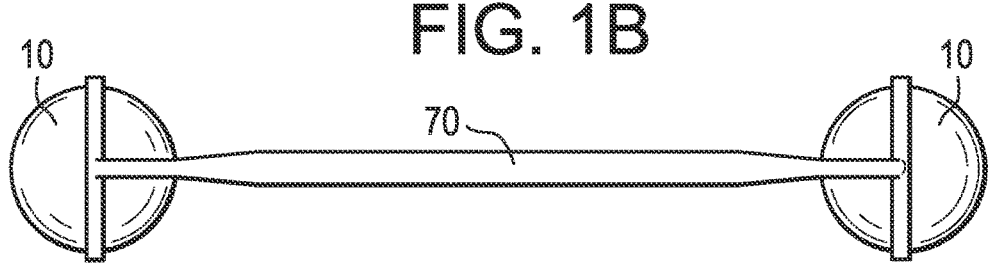

FIG. 3A
FIG. 3B
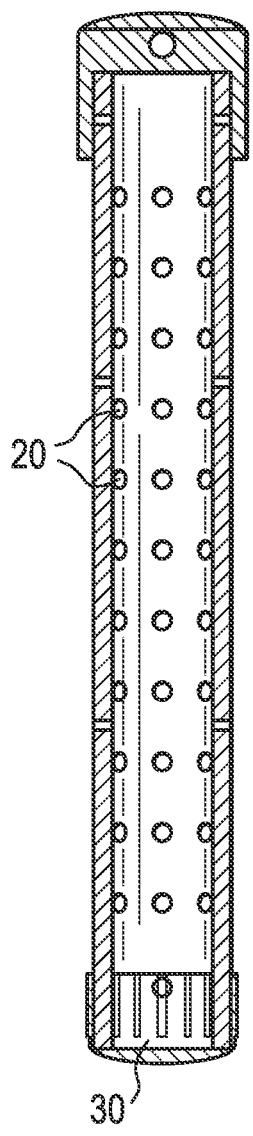
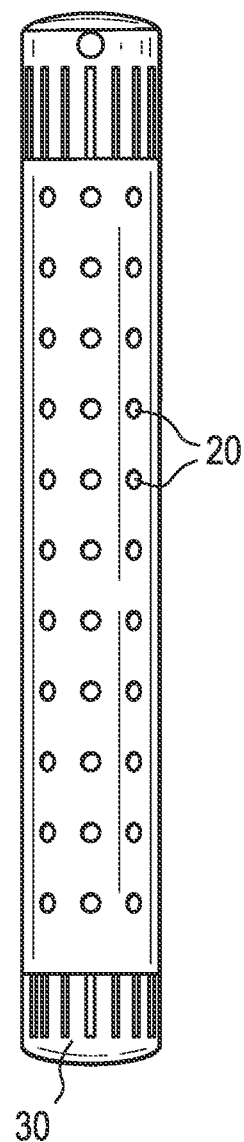

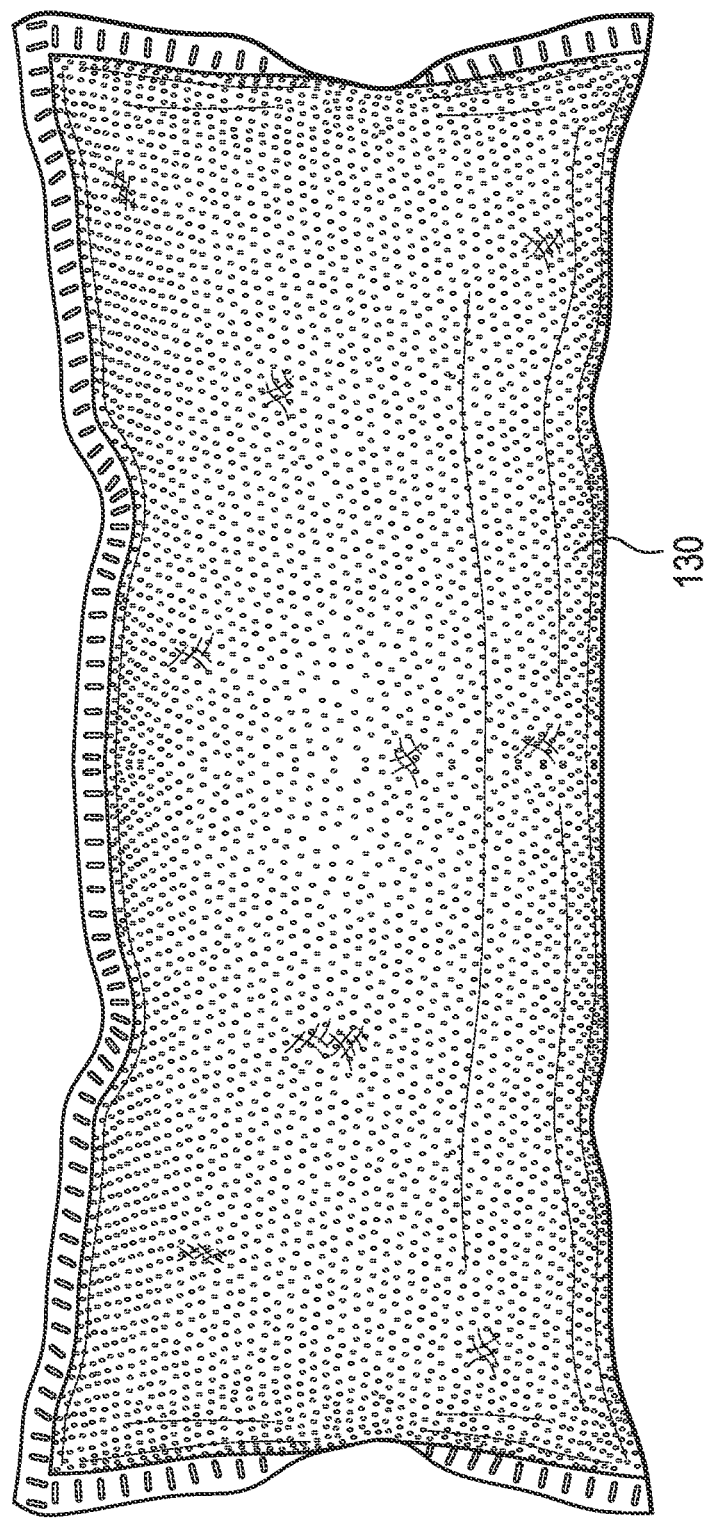

DEODORIZING GLOVE HOLDER FOR ATHLETIC GLOVES AND OTHER EQUIPMENT

CROSS-REFERENCE TO RELATED APPLICATION

This is a continuation of application Ser. No. 15/626,257 filed Jun. 19, 2017, which is a continuation of application Ser. No. 14/856,616 filed Sep. 17, 2015, which claims benefit of provisional applications 62/052,110, filed Sep. 18, 2014, and 62/147,837, filed Apr. 15, 2015, the contents of all of which are incorporated herein by reference in their entirety.

FIELD OF THE INVENTION

This invention relates generally to the field of deodorizers for athletic gloves, and has uses in other athletic equipment as well as non-athletic gloves and shoes.

BACKGROUND OF THE INVENTION

Protective gloves for sports such as Lacrosse, Hockey and Boxing are expensive and once properly broken-in, they can be difficult to replace. When gloves that are primarily made from leathers are dampened with sweat from frequent use they produce an odor. Bacteria in the right environment will grow rapidly. Odor is created when bacteria degrades the sweat components. Gloves of this type are difficult to clean and rid of odor causing bacteria and mildew without compromising the equipment itself. If you wash leather gloves, the integrity of the shape is difficult to maintain. Therefore most athletes just consider the smell to be something they have to deal with.

Some existing products are designed only to deodorize, and use, for example, a cedar filling that is not replaceable. Once the cedar filling has lost its ability to deodorize, the user must replace the entire unit. This approach is bulky, heavy and has no reasonable way of attaching the gloves to the product, therefor preventing it from being a viable glove carrier. This approach is also difficult to attach to other athletic equipment such as a lacrosse stick. Other approaches in the past are not portable and/or require batteries or an alternate power source. And yet other approaches use deodorant inside a housing to mask the odors, without effectively attacking the source of the odors.

SUMMARY OF THE INVENTION

It is therefore an object of the invention to provide a deodorizing insert that kills the bacteria that causes odors in sports equipment as well as other shoes and gloves. It is a further object of the invention to provide a deodorizing insert that absorbs moisture to reduce the chance of bacterial growth within the sports equipment.

In accordance with a preferred embodiment, an outer housing includes removable and replaceable deodorizers, such as silica to absorb moisture. The outer housing includes ventilation holes and is infused with silver ions or other antimicrobial treatments to kill odor causing bacteria.

In a preferred embodiment, each insert is shaped as a stick and has removable and replaceable deodorizers in the shaft of the perforated sticks. There is a handle connecting the two sticks along with a wrist guard clip designed to secure the gloves to the inserts. The gloves can then be stored in the equipment bag or using the handle and in the example of Lacrosse or Hockey can be slid over the handle of the Lacrosse/Hockey stick and transported that way. Either way while the gloves are not being used they are being deodorized—removing the smell/moisture and bacteria while not compromising the shape or comfort of the glove to the athlete.

BRIEF DESCRIPTION OF THE DRAWINGS

A full and enabling disclosure of the embodiments of the present invention, including the best mode thereof, directed to one of ordinary skill in the art, is set forth more particularly in the remainder of the specification, which makes reference to the appended FIGS., in which:

FIG. 1A illustrates a prospective front view of an embodiment of deodorizing sticks.

FIG. 1B illustrates a top view of the handle and bottom locking caps according to one embodiment.

FIG. 3A and FIG. 3B illustrate a prospective front view of perforated shafts according to one embodiment.

FIG. 6 illustrates a top view of an insert according to one embodiment.

DETAILED DESCRIPTION OF PREFERRED EMBODIMENTS OF THE INVENTION

Figure 2:
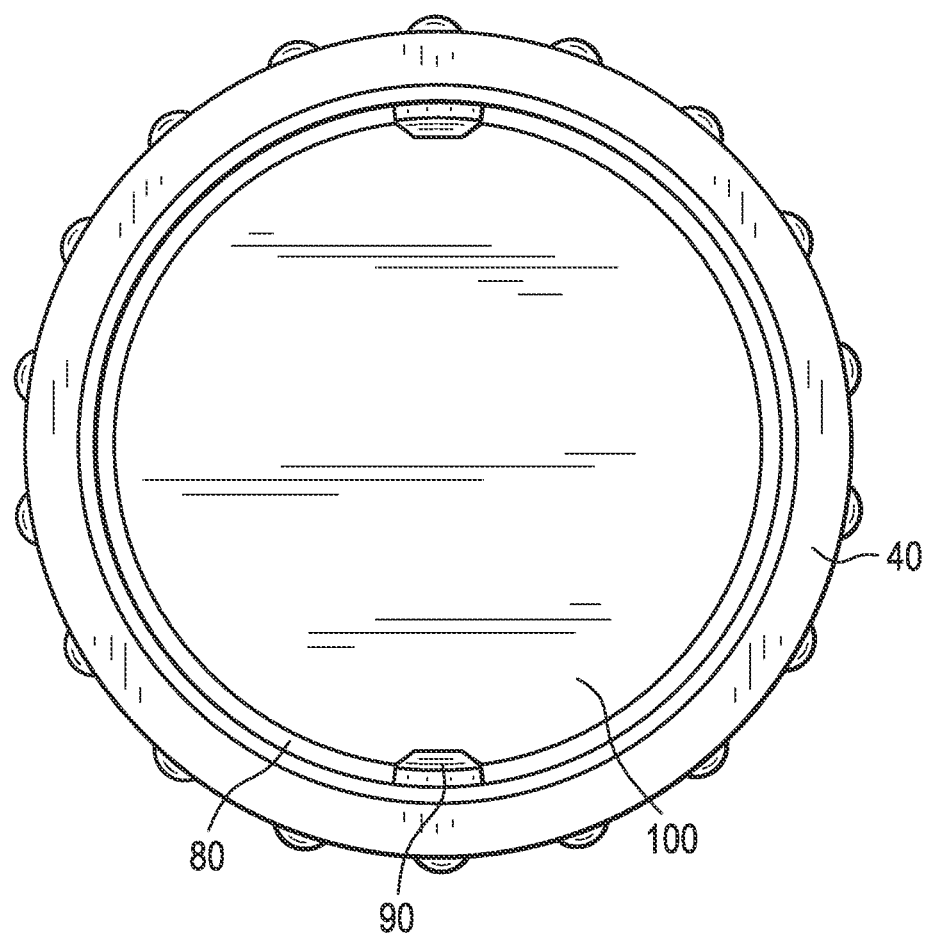
FIG. 2 illustrates a top view of an interlocking mechanism of a deodorizing stick according to one embodiment.

The embodiments in FIGS. 1-6 illustrate embodiments that are intended for use by individuals who wish to deodorize athletic gloves by removing the smell and/or moisture and bacteria of the gloves. These concepts of these embodiments can be also be used for athletic shoes and non-athletic gloves and shoes.

FIG. 1A illustrates a front view of an embodiment in a stick shape. Each stick has a removable top cap (30) and a bottom locking cap (10). In this embodiment, the removable cap (30) interlocks with the outer housing shaft (40) in order to remove and replace the deodorizing and moisture absorbing removable insert (130) when needed. The bottom locking cap (10) can be permanently attached to outer housing shaft (40) in order for handle (70) to be secure. The outer housing shaft (40) has ventilation holes (20) so that air can travel in and out of the stick. This design allows the deodorizing and moisture absorbing material in the moisture absorbing removable insert (130) to effectively remove the moisture and odor from the glove without having direct contact with the glove. In this embodiment, the handle (70) is braided. Alternate embodiments include fixed hard plastic handles or a solid connection between the sticks. The handle (70) connects the first deodorizing stick (140) and second deodorizing stick (150). The handle (70) also can be used to transport the sticks or for storing. The wrist guard clip (50) attaches to the both sides of the handle (70) by an elastic bungee cord (60). The wrist guard clip (50) secures the sticks to the athletic gloves and prevents the gloves from sliding off of the first (140) and second deodorizing sticks (150). For example, when used with Lacrosse gloves, the two sticks can be inserted into the two gloves, and the elastic bungee cord (60) can be connected between the two sticks in a manner that includes the player's Lacrosse stick (not shown) inside the loop created by the handle (70) and the elastic bungee cord (60). This allows the player to carry the gloves on the Lacrosse stick. Similar connection and carrying concepts can be used with other sports equipment as well.

FIG. 1B illustrates a top view of the first deodorizing stick (140) and second deodorizing stick (150) connected by the handle (70).

FIG. 2 illustrates a top view of the interlocking mechanism used to secure and attach the removable cap (30) to the outer housing shaft (40). In this embodiment, the outer housing shaft (40) interlocks with the removable cap (30) by means of an indented notch (90) on the inner housing cap (80), as shown in FIG. 4. However, alternative configurations can be used to provide an interlocking mechanism in order to attach and remove the removable cap (30). The removable insert (130) can be removed and replaced in the opening aperture (100) as shown in FIG. 4. This embodiment uses a screw off design. Alternate embodiments include utilizing a screw top or access point on the top of the outer housing shaft (40) or inner housing cap (80) where the handle (70) affixes to the outer housing shaft (40).

FIGS. 3A and 3B illustrate a streamlined view of the deodorizing stick. FIG. 3A illustrates an alternate embodiment where the tube width is adjusted to align with the bottom locking cap (10) and removable top cap (30).

Figure 4A:
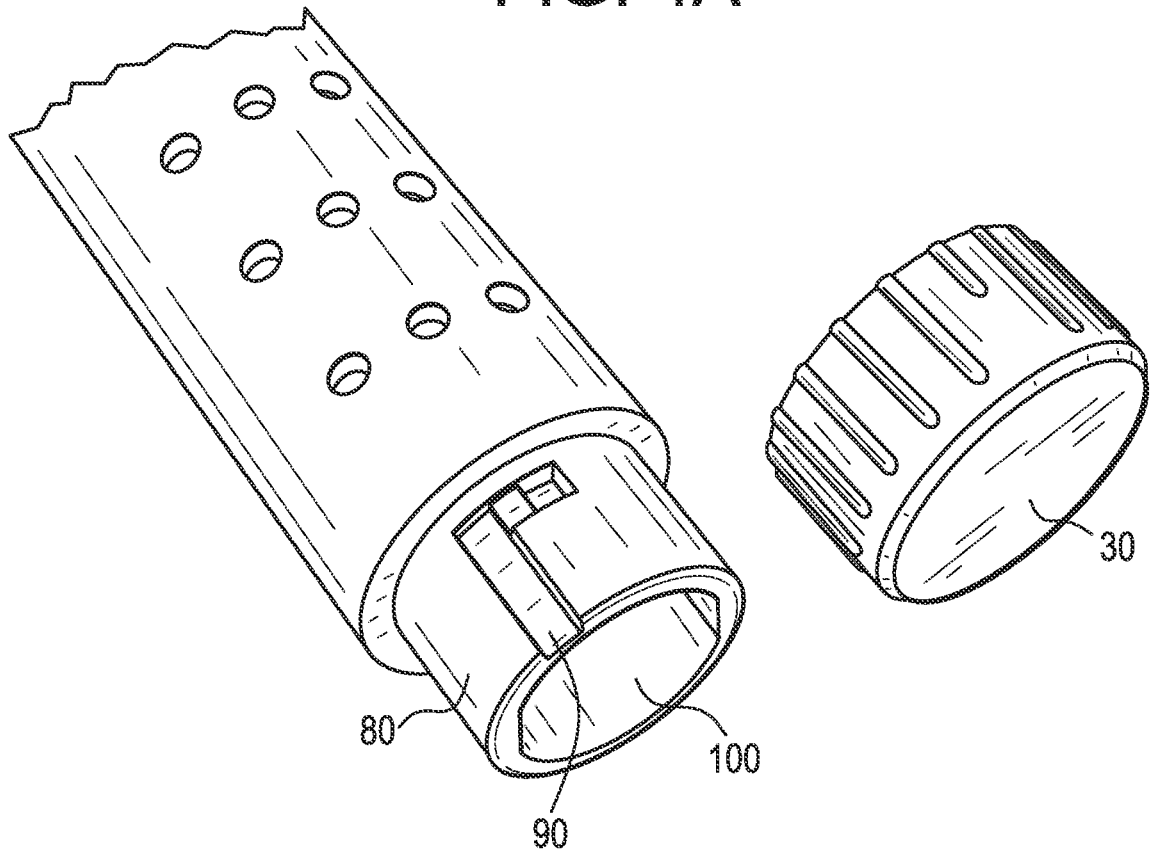
FIG. 4A and FIG. 4B illustrate a side view of a perforated shaft and interlocking mechanism according to one embodiment.
Figure 4B:
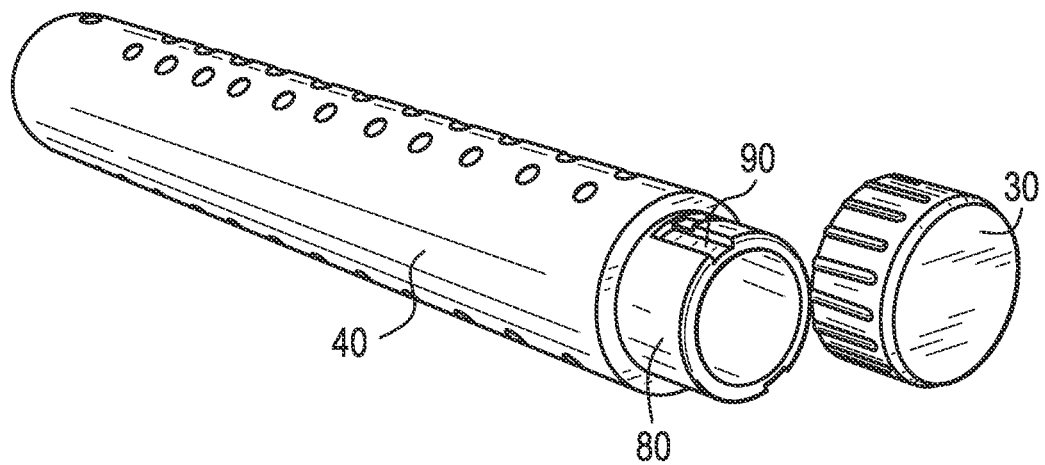

FIGS. 4A and 4B illustrate a side view of the interlocking mechanism used to remove and replace the insert (130) when needed. The figure illustrates the removable top cap (30) detached from the outer housing shaft (40). In the preferred embodiment, the outer housing shaft (40) interlocks with the removable cap (30) by means of an indented notch (90) on the inner housing cap (80). The removable top cap (30) can be either attached to the outer housing shaft (40) or detached to the outer housing shaft (40). This removable cap (30) allows the user to remove and replace the removable insert (130) when needed. Alternate embodiments include such as using a flip cap, or rubber slip cap may be used to remove the removable cap (30).

Figure 5A:
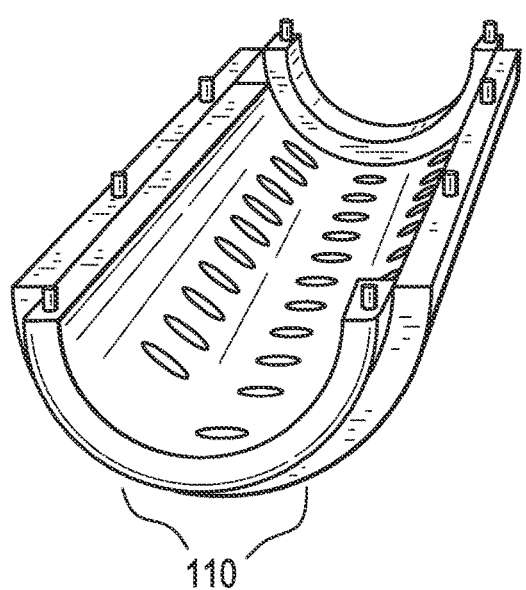
FIG. 5A and FIG. 5B illustrate a side view of each half of a perforated shaft according to one embodiment.
Figure 5B:
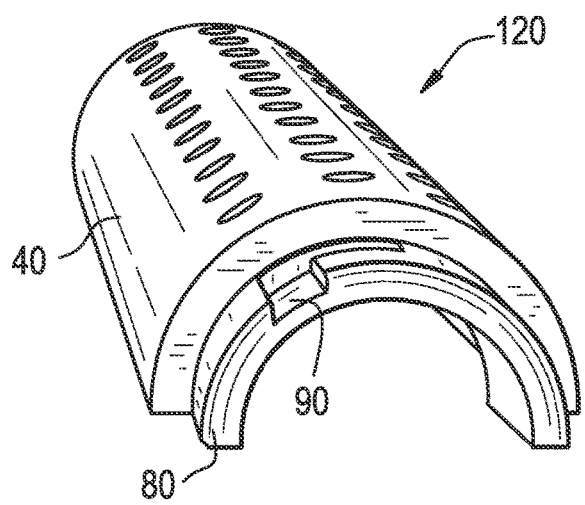

FIGS. 5A and 5B illustrate a side view of the first half (110) of the outer housing shaft (40) and the second half (120) of the outer housing shaft (40). This view illustrates the configuration of the outer housing shaft (40) in which the ventilation holes (20) are designed to help diffuse the deodorizer in the removable insert (130) into the glove to remove the odor from the glove.

FIG. 6 illustrates a top view of the removable insert (130). In this embodiment, the insert contains approximately 7.5 grams of scented silica gel plus 7.5 grams of activated carbon to effectively remove the smell, moisture, and bacteria from the user's glove while not compromising the shape or comfort of the glove to the user. It has been found that this ratio and amount provides effective moisture removal without an overbearing fragrance for athletic equipment. In this embodiment, the removable insert (130) has a width of approximately 2 cm and a length of 18 cm. However, alternate embodiments may include measurements in which the removable insert (130) is shaped appropriately to fit inside the shape of the stick or other shaped deodorizing insert.

Figure 7:
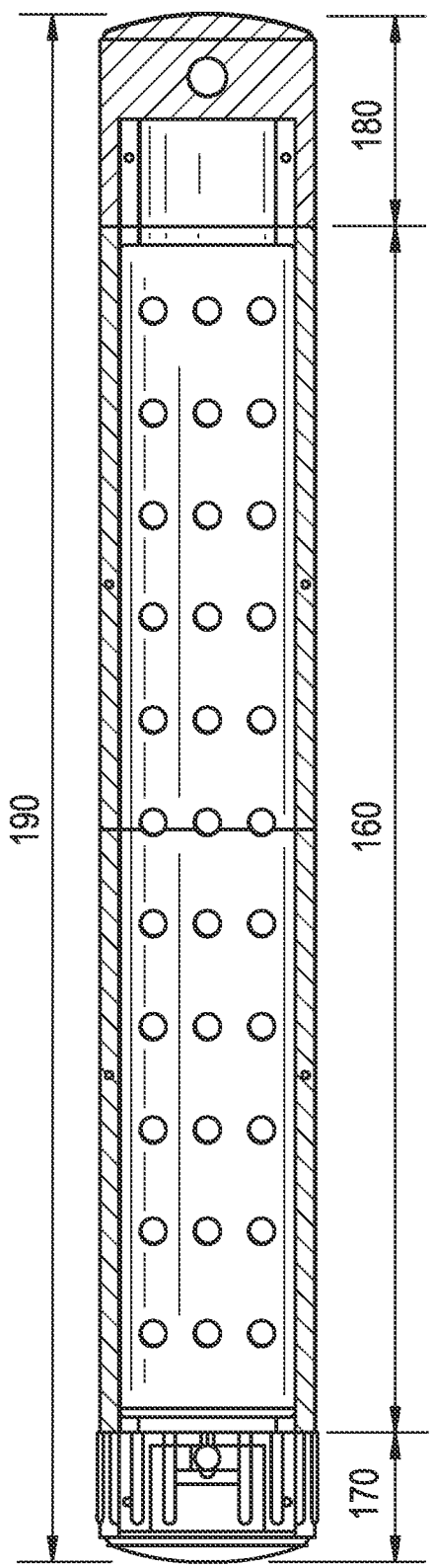
FIG. 7 illustrates measurements of a deodorizing stick according to one embodiment.

FIG. 7 illustrates the dimensions of a deodorizing stick in one embodiment. Distance A (160) illustrates that the distance between the bottom locking cap (10) and removable top cap (30) is about 156 mm. Distance B (170) illustrates the length of the removable top cap, which is about 17 mm. Distance C (180) illustrates the length of the bottom locking cap, which is about 27 mm. Distance D (190) illustrates the length of the entire deodorizing stick, which is about 200 mm. Dimensions of an embodiment of the stick can be roughly 7 and ½ inches long, ¾ of an inch wide and connected by a cord handle that is roughly 6 inches long.

In addition to having deodorizing replaceable inserts (130), the plastic used to create the stick can be infused with an antimicrobial solution such as the commercially available Silver Shield (Tm) Antimicrobial solution. By embedding the plastic with this solution or other silver ion solutions, the embedded plastic itself can inhibit the growth of odor causing bacteria. Of course, the antimicrobial product is not limited to Silver Shield. Other suitable antimicrobial products may be used. Embodiments can also be used without the handle in appropriate applications, and the invention is not limited to any particular size, as it may be shortened or lengthened to fit many size products.

The embodiments described above and variations thereof can be used as a pair or separately to deodorize, absorb moisture, and fight bacteria in volleyball knee pads, soccer shin guards, elbow pads, all types of active shoes, cleats, ski boots, cowboy boots and boots for recreational purposes. These embodiments may be inserted into a bag or used in conjunction with a perforated bag or perforated antimicrobial bag to prevent odor, absorb moisture and fight bacteria.

ADDITIONAL DETAILS AND DIMENSIONS OF A PREFERRED EMBODIMENT INCLUDE

Tube (but not limited to this material or shape)
Material: ABS Plastic with Injected Silver Seal
Parts:
1. Tube
2. Top Cap
3. Bottom Locking Cap
Handle (but not limited to this material)
Material: Woven Paracord, Elastic, Aluminum
Parts:
1. Paracord handle (~6 inches in length) (handle could be longer or shorter depending on use)
2. Elastic Bungee Cord
3. Aluminum Snap Clip
Insert (but not limited to this material or ingredients)
Material: 7.5 g scented silica gel+7.5 g activated carbon
Dimensions: 2 cm (W)×18 cm (L)

What is claimed is:

1. A deodorizing device comprising:
an enclosure shaped as a tube and having ventilation holes and two caps, at least one of the caps being a removable cap, said enclosure being comprised of plastic that is infused with antimicrobial ions and configured without lateral extensions that restrict the enclosure from contacting a surface of an item to be deodorized;
a removable insert displaced within said enclosure, said insert including a moisture absorbing deodorizer.

2. A device according to claim 1, wherein said ions include silver ions.

3. A pair of devices according to claim 1, further comprising a strap connecting said pair of devices to each other.

4. A pair of devices according to claim 3, further comprising a clip strap connected to one of said devices with a clip at the other end of the clip strap for connecting to said other device.

5. A pair of devices according to claim 3, wherein said strap is made from paracord.

6. A device according to claim 1, wherein said enclosure is approximately 7.5 inches in length and ¾ inches wide.

7. A device according to claim 6, wherein said removable insert includes approximately 50% scented silica and approximately 50% unscented silica.

8. A device according to claim 7, wherein said removable insert is approximately 18 cm long and approximately 2 cm wide.

9. A device according to claim 6, wherein said removable insert includes approximately 7.5 g scented silica gel and approximately 7.5 g activated carbon.

10. A device according to claim 1, wherein said enclosure maintains a formed shape, and said removable insert is a container that includes said moisture absorbing deodorizer.

11. A device according to claim 1, wherein at least one of the caps is wider than the remainder of the enclosure.

12. A device according to claim 1, wherein said plastic comprises ABS plastic.

13. A device according to claim 1, Wherein at least one of the at least one removable cap attaches to the enclosure via an indented notch and groove mating between the inside surface of the at least one of the at least one removable cap and the enclosure.

14. A device for insertion within sports equipment comprising:
a cylindrical enclosure having ventilation holes extending over about 156 mm of the cylindrical enclosure, the cylindrical enclosure having two caps, at least one of the caps being a removable cap, the cylindrical enclosure being comprised of plastic that is infused with antimicrobial ions and configured without lateral extensions that restrict the cylindrical enclosure from resting on an internal surface of the sports equipment when inserted into the sports equipment;
a removable insert displaced within said cylindrical enclosure, said insert including a moisture absorbing deodorizer.

15. A device according to claim 14, wherein at least one of the at least one removable cap attaches to the cylindrical enclosure via an indented notch and groove mating between the inside surface of the at least one of the at least one removable cap and the cylindrical enclosure.

16. A pair of devices according to claim 14, further comprising a strap connecting said pair of devices to each other.

17. A system including:
a sports equipment;
an enclosure shaped as a tube and having ventilation holes and two caps, at least one of the caps being a removable cap, said enclosure being comprised of plastic that is infused with antimicrobial ions and inserted into the sports equipment and contacting an internal surface of the sports equipment;
a removable insert displaced within said enclosure, said insert including a moisture absorbing deodorizer.

* * * * *